United States Patent [19]

Dralle-Voss et al.

[11] Patent Number: 5,663,435
[45] Date of Patent: Sep. 2, 1997

[54] REACTION PRODUCTS OF AMINOALKYLENECARBOXYLIC ACIDS AND MINERAL OIL MIDDLE DISTILLATES WHICH CONTAIN THEM

[75] Inventors: Gabriele Dralle-Voss, Darmstadt; Knut Oppenländer, Ludwigshafen; Klaus Barthold, Mannheim; Bernd Wenderoth, Birkenau; Wolfgang Kasel, Nussloch, all of Germany

[73] Assignee: BASF Aktiengesellschaft, Ludwigshafen, Germany

[21] Appl. No.: 549,668

[22] PCT Filed: Jun. 29, 1994

[86] PCT No.: PCT/EP94/02122

§ 371 Date: Nov. 29, 1995

§ 102(e) Date: Nov. 29, 1995

[87] PCT Pub. No.: WO95/03378

PCT Pub. Date: Feb. 2, 1995

[30] Foreign Application Priority Data

Jul. 21, 1993 [DE] Germany ............... 43 24 394.0

[51] Int. Cl.$^6$ ............... C07C 233/05; C07C 229/22; C10L 1/22

[52] U.S. Cl. ............... 564/153; 44/387; 44/399; 44/408; 44/418; 44/419; 560/24; 560/25; 560/39; 560/41; 560/157; 560/158; 560/159; 560/169; 560/170; 560/171; 564/152

[58] Field of Search ............... 44/408, 418, 419, 44/399, 387; 564/153, 152; 560/169, 170, 171, 157, 158, 159, 24, 25, 39, 41

[56] References Cited

U.S. PATENT DOCUMENTS

| | | | |
|---|---|---|---|
| 3,024,277 | 3/1962 | Hotten et al. | 44/408 |
| 5,071,445 | 12/1991 | Oppenlaender et al. | 44/408 |
| 5,194,068 | 3/1993 | Mohr et al. | 44/391 |

FOREIGN PATENT DOCUMENTS 0301448  2/1989  European Pat. Off. .

*Primary Examiner*—Shailendra Kumar
*Attorney, Agent, or Firm*—Oblon, Spivak, McClelland, Maier & Neustadt, P.C.

[57] ABSTRACT

Reaction products of amino-alkylenecarboxylic acids with polyoxyalkylene compounds are used as paraffin dispersants for mineral oil middle distillates.

4 Claims, No Drawings

REACTION PRODUCTS OF AMINOALKYLENECARBOXYLIC ACIDS AND MINERAL OIL MIDDLE DISTILLATES WHICH CONTAIN THEM

This application is a 371 of PCT/EP94/02122 filed Jun. 29 1994.

BACKGROUND OF THE INVENTION

1. Field of the Invention

The present invention relates to reaction products of aminoalkylenecarboxylic acids, which products are suitable as paraffin dispersants, and their use and mineral oil middle distillate compositions which are based on a hydrocarbon mixture and contain these reaction products.

2. Discussion of the Background

Middle distillates, for example gas oils, diesel oils or fuel oils, which are obtained by distillation of mineral oils, have different paraffin contents, depending on the origin of the crude oil. At relatively low temperatures, solid paraffins separate out (cloud point, CP). On further cooling, the lamellar n-paraffin crystals form a house-of-cards structure and the middle distillate sets although the predominant part of the middle distillate is still liquid. The flow of the mineral oil middle distillates is considerably adversely affected by the precipitated n-paraffins between the cloud point and the pour point. The paraffins block filters and cause irregular fuel feed to the combustion units or completely stop this feed.

It has long been known that the crystal growth of the paraffins in the mineral oil middle distillates can be modified by suitable additives. Effective additives on the one hand prevent middle distillates from forming such house-of-cards structures and becoming solid at temperatures a few degrees Centigrade below the temperature at which the first paraffin crystals crystallize out and, on the other hand, result in the formation of fine, well crystallized, separate paraffin crystals which pass through filters in motor vehicles and heating systems or at least form filter cakes which are permeable to the liquid part of the middle distillates, thus ensuring trouble-free operation.

A disadvantage of this prior art is based on the fact that the precipitated paraffin crystals have a higher density than the liquid part and therefore tend to settle out on the bottom of the container to an increasing extent during storage. This results in the formation of a homogeneous phase having a low paraffin content in the upper part of the container and a two-phase paraffin-rich layer at the bottom. Since the middle distillate is generally taken off slightly above the bottom of the container both in vehicle tanks and in the storage and delivery tanks of mineral oil dealers, there is a danger that the high concentration of solid paraffins will lead to blockage of filters and metering means. This danger is all the greater the further the storage temperature is below the precipitation temperature of the paraffins (cloud point), since the amount of paraffin precipitated is a function of the temperature and increases with decreasing temperature.

The paraffin crystal modifiers, ie. is flow improvers, are polymers which change the crystal growth of the n-paraffins by cocrystallization (interaction). The flow properties of the middle distillate at relatively low temperatures are advantageously affected. The efficiency of the flow improvers is expressed indirectly by measurement of the cold filter plugging point (CFPP), according to DIN 51,428.

Conventional ethylene copolymers, especially copolymers of ethylene and unsaturated esters, are used as low-temperature flow improvers. DE 11 47 799 and DE 19 14 756 describe, for example, copolymers of ethylene with vinyl acetate, containing from 25 to 45% by weight of vinyl acetate or vinyl propionate and having a molecular weight of from 500 to 5,000.

Furthermore, GB 2 095 698 discloses that a combination of the stated copolymers with amides of long-chain amines and aromatic or cycloaliphatic carboxylic acids can be added to middle distillates.

However, these mixtures are still unsatisfactory with regard to the dispersing properties of the precipitated paraffins. It is therefore necessary for the additives introduced also to effect dispersing of the precipitated paraffins.

EP-A 398 101 discloses reaction products of aminoalkylenepolycarboxylic acids with long-chain secondary amines, which have been completely reacted with the amines to give the amide or ammonium salt, as paraffin dispersants.

The non-prior-published German Application P 4237662.9 relates to reaction products of aminoalkylenepolycarboxylic acids of long-chain secondary amines, in which free carboxyl groups or alkali metal or alkaline earth metal carboxylate groups are still present.

These paraffin dispersants are commercially available in general in the form of a concentrated solution in oil-soluble solvents, such as high-boiling petroleum ethers or mixtures of aromatics. However, in concentrated solution, these dispersants may have such a high pour point that they are more difficult to handle during transfer or metering.

SUMMARY OF THE INVENTION

It is an object of the present invention to provide paraffin dispersants for mineral oil middle distillates, which dispersants have a good dispersing action as well as a low pour point in concentrated solution.

We have found that this object is achieved by the compounds of the formulae I and II

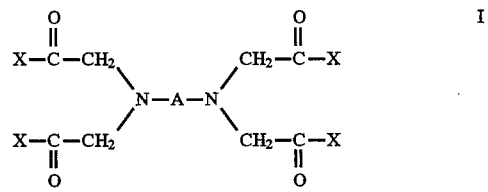

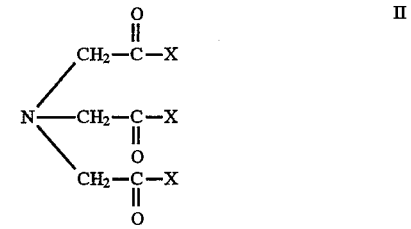

where

A is straight-chain or branched alkylene of 2 to 6 carbon atoms or a radical of the formula III

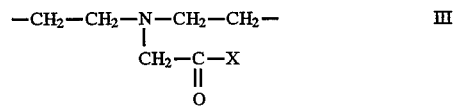

X is

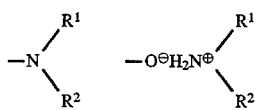 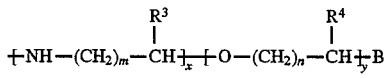

and/or a radical of the formula IV

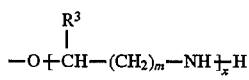 IV where $R^1$ is hydrogen or a straight-chain aliphatic $C_{10}$–$C_{30}$ radical, $R^2$ is a straight-chain aliphatic $C_{10}$–$C_{30}$ radical, $R^3$ and $R^4$ are each hydrogen, methyl or ethyl, m and n are each from 1 to 5, x is from 0 to 3, y is from 1 to 100 and B is hydroxyl or $C_1$–$C_{30}$-alkoxy or is naphthyloxy or phenoxy which is unsubstituted or monosubstituted to trisubstituted by $C_1$–$C_{18}$-alkyl, or is $C_1$–$C_{30}$-alkylcarboxy or $C$–$C_{30}$-alkenylcarboxy, or is amino which is monosubstituted by a straight-chain aliphatic $C_1$–$C_{30}$ radical, or is amino which is disubstituted by straight-chain aliphatic $C_1$–$C_{30}$ radicals, or is $C_1$–$C_{30}$-alkylamido or alkenylamido or a group of the formula V $$-O+CH-(CH_2)_m-NH+_xH \quad \overset{R^3}{|}$$ V where the variables have the abovementioned meanings, with the proviso that X is a) at least one

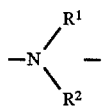

group and b) at least one group of the formula IV, both conditions being fulfilled.

We have also found the use of the compounds I and II as paraffin dispersants, and mineral oil middle distillates which contain these compounds.

DETAILED DESCRIPTION OF THE PREFERRED EMBODIMENTS

The reaction of ethylenetriaminetetraacetic acid, diethylenetriaminetetraacetic acid or nitrilotriacetic acid with amines $HNR^1R^2$ leads to compounds of the formula I or II, where X is —$NR^1R^2$ or the corresponding ammonium salt —$O^{\ominus}H_2N^{\oplus}R^1R^2$. $R^1$ and $R^2$ are each a straight-chain aliphatic $C_{10}$–$C_{30}$ radical, preferably a $C_{14}$–$C_{22}$ radical and $R^1$ may furthermore be hydrogen. $R^1$ and $R^2$ are each particularly preferably a straight-chain aliphatic $C_{10}$ –$C_{30}$ radical, in particular a $C_{14}$ –$C_{22}$ radical, ie. amines used for the preparation of the compounds I and II are secondary amines. Specific examples of secondary amines are dioleylamine, di-tallow fatty amine, dipalmitylamine, di-coconut fatty amine and dibehenylamine and preferably distearylamine or hydrogenated di-tallow fatty amine (the latter being of 16 to 18 carbon atoms).

The groups of the formula IV are incorporated in the paraffin dispersants I and II by reaction of the compounds VI with the stated polycarboxylic acids.

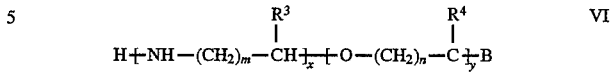 VI

The compounds VI are polyoxyalkylene derivatives. $R^3$ and $R^4$ are each hydrogen, methyl or ethyl. m and n are each from 1 to 5. The compounds are thus obtainable by polymerization of alkylene oxides, such as ethylene oxide, propylene oxide or butylene oxide, or by ring cleavage of tetrahydrofuran with polymerization. x and y indicate the degree of polymerization. x is from 0 to 5, preferably 0, and y is from 1 to 100, preferably from 1 to 20. If B is hydroxyl, the compounds VI are polyalkylene glycols, such as polyethylene glycol or polypropylene glycol, polytetrahydrofuran compounds or mixed copolymers of, for example, ethylene oxide and propylene oxide. In general, the average molecular weight of the glycols is from 200 to 4,000.

Alkoxylated alcohols are also suitable compounds VI. In this case, B is straight-chain or branched $C_1$–$C_{30}$-alkoxy, preferably a $C_8$ –$C_{22}$ radical. They are derived from the corresponding alcohols, such as isotridecanol, isodecanol, decanol, tallow fatty alcohol and stearyl alcohol.

The compounds VI furthermore comprise alkoxylated phenols and naphthols, which are unsubstituted or monosubstituted to trisubstituted by $C_1$ –$C_{18}$-alkyl. In this class of compounds, B is derived, for example, from p-cresol, di-tert-butylphenol, isooctylphenol, isononylphenol or β-naphthol.

Compound VI is an alkoxylated carboxylic acid if B is $C_1$ –$C_{30}$-alkylcarboxy or $C_1$–$C_{30}$-alkenylcarboxy. The carboxylic acids are preferably straight-chain acids of 8 to 22 carbon atoms, such as stearic acid, lauric acid, oleic acid, behenic acid, tallow fatty acid, 2-ethyl-hexanoic acid or isononanoic acid.

B may furthermore be amino which is mono-substituted or disubstituted by aliphatic $C_1$–$C_{30}$ radicals, preferably $C_{10}$–$C_{22}$ radicals. These amino radicals are derived from amines such as behenylamine, distearylamine, di-tallow fatty amine or hydrogenated di-tallow fatty amine.

Finally, B may be $C_1$–$C_{30}$-alkylamido or $C_1$–$C_{30}$-alkenylamido, such as the radicals of stearylamide and oleamide.

If, in the compounds VI, x is greater than zero, all stated polyoxyalkylene compounds are present in aminated form. This amination can be carried out in a known manner by aminating hydrogenation or aminopropylation of the corresponding hydroxy compounds. If polyglycols are aminated at both chain ends, compounds VI in which B is of the formula V are obtained.

Compounds I which carry three radicals —$NR^1R^2$ and one radical of the formula IV are preferred.

For the preparation of the compounds I and II, the polycarboxylic acids, at least 1 equivalent of the amines $HNR^1R^2$ and at least 1 equivalent of the compounds VI may be mixed and heated to 100°–200° C., and the water of reaction can be distilled off continuously. The reaction is preferably carried out in the presence of a catalytic amount of an acid such as toluenesulfonic acid.

The novel compounds can be used as paraffin dispersants. They may be added to mineral oil middle distillates, preferably those having an initial boiling point above 160° C. and a final boiling point below 420° C.

The compounds of the formulae I and II are added to mineral oil middle distillate compositions as a rule in amounts of from 25 to 1,000 ppm, preferably from 50 to 500 ppm.

The middle distillates usually already contain conventional flow improvers which are described in detail in the patent literature, for example in DE 19 14 756 and EP-A 486 836 (ethylene/vinyl ester copolymers and mixtures thereof with other copolymers), EP 214 876 (α-olefin/maleic anhydride ester) or EP 155 807 (alkyl fumarate/vinyl acetate copolymers).

However, terpolymers which contain further comonomers in addition to ethylene and vinyl esters or acrylates are also suitable. The molecular weight of these flow improvers is as a rule from 500 to 5,000, preferably from 1,000 to 3,000. Mixtures of different flow improvers are also suitable.

The middle distillates can, if required, also contain a conductivity improver, as described, for example, in DE-A 21 16 556. In addition to good dispersing properties, the compounds I and II have the advantage of possessing a low pour point in high concentration in oil-soluble solvents.

EXAMPLES

A) Preparation of the Aminoalkylenepolycarboxamides and -Esteramides (Compound I)

General Preparation Method for the Paraffin Dipsersants PD1-PD8

151.5 g (0.3 mol) of distearylamine, 0.1 mol of compound VI and about 1.1 g of p-toluenesulfonic acid were initially taken and melted. At 100°–110° C., 29.5 g (0.1 mol) of ethylenediaminetetraacetic acid were added. The reaction mixture was heated to 190° C. under a nitrogen atmosphere and condensed at this temperature until the acid number had fallen below 10 mg KOH/g. The water of reaction distilled off completely during this procedure. After filtration, a brown waxy solid was obtained.

All compounds exhibited the typical amide band at 1650 $cm^{-1}$ in the IR spectrum. The amidoester additionally exhibited an ester band at 1730 $cm^{-1}$.

PD1: Reaction product of ethylenediaminetetraacetic acid, distearylamine and ethoxylated isononylphenol (molecular weight: 490 g/mol, degree of ethoxylation: 6) in a molar ratio of 1:3:1.

PD2: Reaction product of ethylenediaminetetraacetic acid, distearylamine and ethoxylated isononylphenol (molecular weight: 578 g/mol, degree of ethoxylation: 8) in a molar ratio of 1:3:1.

PD3: Reaction product of ethylenediaminetetraacetic acid, distearylamine and polyethylene glycol (molecular weight: 200 g/mol) in a molar ratio of 1:3:1.

PD4: Reaction product of ethylenediaminetetraacetic acid, distearylamine and polyethylene glycol (molecular weight: 300 g/mol) in a molar ratio of 1:3:1.

PD5: Reaction product of ethylenediaminetetraacetic acid, distearylamine and N-(2-hydroxy-1-methylethyl)-distearylamine in a molar ratio of of 1:3:1.

PD6: Reaction product of ethylenediaminetetraacetic acid, distearylamine and polypropylene glycol ether diamine (molecular weight: 2,000 g/mol) in a molar ratio of 1:3:1.

PD7: Reaction product of ethylenediaminetetraacetic acid, distearylamine and N-(hydroxyethyl)-distearylamine in a molar ratio of 1:3:1.

PD8: Reaction product of ethylenediaminetetraacetic acid, distearylamine and propoxylated distearylamine (degree of propoxylation:5 ) in a molar ratio of 1:3:1.

B) Testing of the Mineral Oil Middle Distillate Compositions

The following mineral oil middle distillate compositions were tested:

1) as paraffin dispersant PD:

PD1–PD8 ethylenediaminetetraacetic acid derivatives; as comparison PD9 (ethylenediaminetetraacetamide A1 from EP-A 398 101)

2) as flow improver F1:

F1 (A) ethylene/vinyl propionate (containing about 40% by weight of vinyl propionate) having an average molecular weight of about 2,500 (F1 (A) from EP-A 398 101)

3) as conductivity improver CV: CV (E) from EP-A 398 101.

The middle distillates used for the following dispersing tests were diesel fuels of commercial German refinery quality; they are referred to as DK 1, DK 2 and DK 3:

|  | DK 1 | DK 2 | DK 2 |
|---|---|---|---|
| Cloud point CP (°C.) | −8 | −8 | −7 |
| CFPP (°C.) | −13 | −12 | −10 |
| Density at 20° C. (g/ml) | 0.827 | 0.831 | 0.829 |
| Initial boiling point (°C.) | 165 | 175 | 183 |
| 20% boiling point (°C.) | 210 | 223 | 211 |
| 90% boiling point (°C.) | 318 | 314 | 317 |
| Final boiling point (°C.) | 358 | 352 | 364 |

Description of the Test Method:

Different amounts of paraffin dispersants PD 1-PD 8 or PD 9 (in each case as a 50% strength solution in Solvesso® 150 (high-boiling mixture of aromatics having a boiling range of from 186° to 206° C., from Esso), flow improver F1 and conductivity improver CV were added to the middle distillates at 40° C. while stirring, and the mixture was then cooled to room temperature.

The middle distillates containing additives were stored in 100 ml measuring cylinders for from 16 to 20 hours in a freezer at −13° C. or at −18° C. The volume of the paraffin phase which had settled out (% by volume) and the appearance of the oil phase were then assessed visually.

The results are shown in Tables I–III. It can be seen that, in the middle distillates, compounds PD 1–PD 8 have a dispersant effect which is just as good as that of comparative compound PD 9.

The advantage of the novel compounds is that their 50% strength solution in a solvent has a lower pour point than the solution of PD 9 (cf. Table. IV), which substantially facilitates handling in practice.

TABLE I

Dispersing test in DK 1, CP: −8° C., CFPP: −13° C.

| PD# | Dose (ppm) | FI (ppm) | CV (ppm) | Temp. (°C.) | Time (h) | Paraffin sediment (% by volume) | Appearance of oil phase |
|---|---|---|---|---|---|---|---|
| 1 | 100 | 200 | 3 | −13 | 16 | 5 | dispersed |
| 1 | 100 | 300 | 3 | −18 | 20 | 0 | dispersed |
| 2 | 100 | 300 | 3 | −18 | 20 | 0 | dispersed |
| 3 | 200 | 200 | 3 | −18 | 20 | 3 | dispersed |
| 4 | 200 | 200 | 3 | −18 | 20 | 5 | dispersed |
| Comparison: | | | | | | | |
| 9 | 100 | 300 | 3 | −18 | 20 | 0 | dispersed |

TABLE II

Dispersing tests in DK 2, CP: −8,C, CFPP: −12° C.

| PD# | Dose (ppm) | FI 1 (ppm) | CV (E) (ppm) | Temp. (°C.) | Time (h) | Paraffin sediment (% by volume) | Appearance of oil phase |
|---|---|---|---|---|---|---|---|
| 1 | 100 | 200 | 3 | −13 | 16 | 5 | dispersed |
| 1 | 100 | 300 | 3 | −18 | 20 | 0 | dispersed |
| 2 | 100 | 300 | 3 | −18 | 20 | 0 | dispersed |
| 5 | 100 | 200 | 3 | −13 | 16 | 0 | dispersed |
| 7 | 100 | 200 | 3 | −13 | 16 | 0 | dispersed |
| Comparison: | | | | | | | |
| 9 | 100 | 300 | 3 | −18 | 20 | 0 | dispersed |

TABLE III

Dispersing tests in DK 3, CP: −7° C., CFPP: −10° C.

| PD# | Dose (ppm) | FI 1 (ppm) | CV (E) (ppm) | Temp. (°C.) | Time (h) | Paraffin sediment (% by volume) | Appearance of oil phase |
|---|---|---|---|---|---|---|---|
| 1 | 100 | 200 | 3 | −13 | 16 | 5 | dispersed |
| 1 | 100 | 300 | 3 | −18 | 20 | 0 | dispersed |
| 2 | 100 | 300 | 3 | −18 | 20 | 0 | dispersed |
| 5 | 100 | 200 | 3 | −13 | 16 | 0 | dispersed |
| 6 | 100 | 200 | 3 | −13 | 16 | 0 | dispersed |
| 7 | 100 | 200 | 3 | −13 | 16 | 0 | dispersed |
| 8 | 100 | 200 | 3 | −13 | 16 | 0 | dispersed |
| Comparison: | | | | | | | |
| 9 | 100 | 300 | 3 | −18 | 20 | 0 | dispersed |

TABLE IV

Pour points of compounds PD 1–PD 7 as 50% strength solutions in Solvesso 150

| PD # | Pour point (°C.) |
|---|---|
| PD 1 | +5 |
| PD 2 | +3 |
| PD 3 | +11 |
| PD 4 | +13 |
| PD 5 | +15 |
| PD 6 | +3 |
| PD 7 | +13 |
| PD 8 | +2 |
| PD 9 (Comparison) | +19 |

We claim:

1. An aminoalkylenecarboxylic acids of the general formula I or II

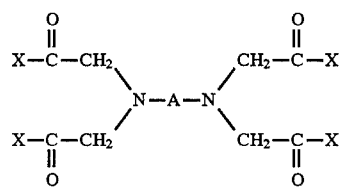

-continued

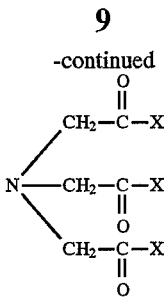

where

A is straight-chain or branched alkylene of 2 to 6 carbon atoms or a radical of the formula III

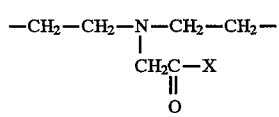

X is

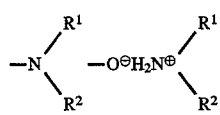

or a radical of the formula IV

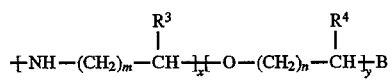

where $R^1$ is hydrogen or a straight-chain aliphatic $C_{10}-C_{30}$ radical, $R^2$ is a straight-chain aliphatic $C_{10}-C_{30}$ radical, $R^3$ and $R^4$ are each hydrogen, methyl or ethyl, m and n are each from 1 to 5, x is from 0 to 3, y is from 1 to 100 and B is hydroxyl or $C_1-C_{30}$-alkoxy or is naphthyloxy or phenoxy which is unsubstituted or monosubstituted to tri-substituted by $C_1-C_{18}$-alkyl, or is $C_1-C_{30}$-alkylcarboxy or $C_1-C_{30}$-alkenylcarboxy, or is amino which is monosubstituted by a straight-chain aliphatic $C_1-C_{30}$ radical, or is amino which is disubstituted by straight-chain aliphatic $C_1-C_{30}$ radicals, or is $C_1-C_{30}$-alkylamido or alkenylamido or a group of the formula V

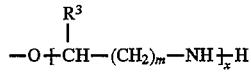

where the variables have the abovementioned meanings, with the proviso that X is a) at least one

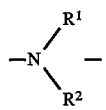

group and b) at least one group of the formula IV, both conditions being fulfilled.

2. A compound as claimed in claim 1, in which $R^1$ is hydrogen or a straight-chain aliphatic radical of 14 to 22 carbon atoms and $R^2$ is a straight chain aliphatic radical of 14 to 22 carbon atoms.

3. A compound of the formula I as claimed in claim 1, in which three radicals X are each

and one radical X is a radical of the formula IV.

4. A composition useful as a paraffin dispersant in mineral oil middle distillates, comprising an effective paraffin dispersant amount of a compound I or II as claimed in claim 1, in a hydrocarbon mixture having an initial boiling point above 160° C. and a final boiling point of below 420° C.

* * * * *